United States Patent [19]

Tranquilla

[11] Patent Number: 5,798,456

[45] Date of Patent: *Aug. 25, 1998

[54] PREDICTING BEHAVIOR OF SYNCHRONOUS FLEXIBLE WEBS

[75] Inventor: Michael N. Tranquilla, Livonia, Mich.

[73] Assignee: Unisys Corp., Blue Bell, Pa.

[*] Notice: The term of this patent shall not extend beyond the expiration date of Pat. No. 5,554,807.

[21] Appl. No.: 752,668

[22] Filed: Nov. 19, 1996

[51] Int. Cl.$^6$ .................................................. G01N 29/12
[52] U.S. Cl. ............................................. 73/579; 73/159
[58] Field of Search ................................. 73/579, 11.04, 73/662, 159, 663

[56] References Cited

U.S. PATENT DOCUMENTS 5,269,181 12/1993 Gibson et al. .......................... 73/579
5,410,906 5/1995 Austin et al. ......................... 73/11.04
5,554,807 9/1996 Tranquilla ............................. 73/579

Primary Examiner—Hezron E. Williams
Assistant Examiner—Nashmiya Fayyaz

[57] ABSTRACT

Disclosed is a method of determining motion-control and damping characteristics for a resilient, multi-element elastomeric belt used in a servo system, yet without need to test in a use environment, this method including: stretching a prescribed length L of the belt between a pair of guide pulleys mounted on a frame with prescribed tension; attaching a prescribed test weight on this length at a prescribed test-distance $L_1$ from one of the guide pulleys; shaking the frame at resonance frequency, sinusoidally; while determining the amplitude of excursion for the weight and the frame; then changing distance $L_1$ and repeating the foregoing operations one or more times.

24 Claims, 10 Drawing Sheets

TENSION-COMPRESSION BAR MODEL

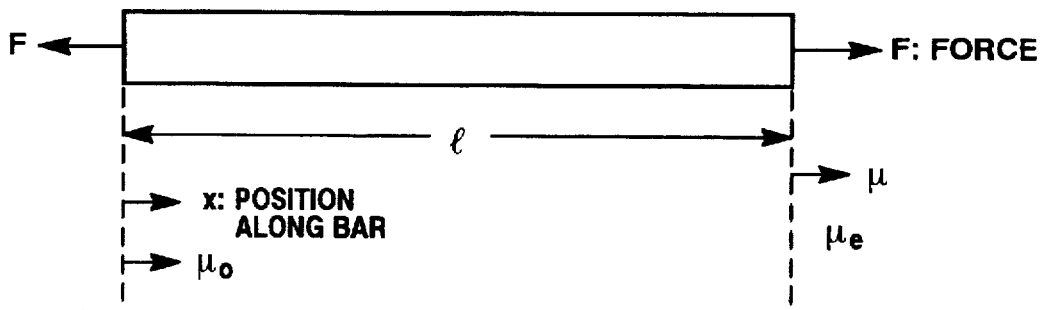

$\mu_0, \mu_e$ : DISPLACEMENTS $$\frac{d\mu}{dx} = \varepsilon, \text{STRAIN}$$

$$\mu = \int_0^x \varepsilon \, dx + \text{CONSTANT}$$

STRESS-STRAIN RELATIONSHIP

$$\sigma = E\varepsilon + q\frac{d\varepsilon}{dt} \quad , \quad \begin{array}{l}\sigma : \text{STRESS} \\ t : \text{TIME}\end{array}$$

E : ELASTIC MODULUS

Q : DAMPING COEFFICIENT $$\sigma = \frac{F}{A} \quad , \text{A : CROSS-SECTIONAL AREA}$$

RESULT:

$$\mu_e - \mu_0 = \frac{F\ell}{AE}\left(1 - e^{-\frac{E}{q}t}\right)$$

*Figure 3A*

LUMPED PARAMETER MODEL c: DASHPOT DAMPING COEFFICIENT k: SPRING STIFFNER $$F_c = c \left( \frac{d\mu_e}{dt} - \frac{d\mu_e}{dt} \right)$$

$$F_K = k (\mu_e - \mu_o)$$

$$F = F_c \div F_k$$

RESULT:

$$\mu_e - \mu_o = \frac{F}{k} \left( 1 - e^{\frac{k}{c}t} \right)$$

COMPARE WITH BAR MODEL

$$k = \frac{AE}{\ell}$$

$$c = \frac{Aq}{\ell}$$

PERFORMING THE SHAKE TEST WITH THE MASS POSITIONED AT SEVERAL LOCATIONS ALONG THE BELT PRODUCES A RANGE OF DATA. A CURVE-FITTING PROCEDURE CAN THEN OPTIMIZE VALUES FOR DAMPING COEFFICIENTS. THIS TENDS TO AVERAGE OUT MEASUREMENT ERRORS AND MINOR IRREGULARITIES IN BELT CONSTRUCTION.

PREDICTING BEHAVIOR OF SYNCHRONOUS FLEXIBLE WEBS

This disclosure involves flexible web lengths for transmitting motion (e.g., synchronous or timing belts) and particularly to tests for determining web characteristics (e.g., damping coefficients)

BACKGROUND, FEATURES

Workers making or using flexible web means (e.g., belts used to transmit motion from one shaft to another) have long been concerned about the complications now typically associated with determining damping characteristics (e.g., damping coefficient) of such a web. Typically, this may involve "trial-and-error" testing of the actual belt in the actual mechanism; or it may require a specific sample size, or it may require that the belt be permanently altered in some way; or "over-stressed" in actual use-environment.

This invention addresses such concerns, and teaches a technique and apparatus for determining such damping coefficients:

without need of trial-error testing of an actual belt length in an actual use-environment, or any associated belt altering or overstressing; and without need of any specific sample size or belt-length (e.g., testing one length can determine damping for many different lengths).

Synchronous belts:

Synchronous flexible webs (sometimes called toothed or timing belts), are increasingly used in high-speed, high-accuracy positioning devices such as computer printers, medical instrumentation, and manufacturing automation equipment. The prime objective in these applications is accurate motion control; e.g., rather than traditional power transmission. Instead of providing continuous motion and constant loads between two shafts, these belts are typically required to transmit complex motions and varying loads with high accuracy.

They are often a component in a servosystem, where their flexibility and damping may affect system bandwidth and stability. This poses a problem for system designers because synchronous-belt manufacturers generally supply only traditional horsepower ratings. They do not provide the stiffness and damping data necessary to perform a more complete mechanism analysis where motion control is the primary concern.

Belt construction complicates the matter. Synchronous belts consist of stranded cords surrounded by an elastomer. The cords, usually glass, steel, or Kevlar, provide strength and stiffness. The elastomer, usually neoprene or urethane (and sometimes coated with nylon), protects the cords, forms the molded teeth, and holds the assembly together. This complex construction makes it difficult to accurately calculate belt stiffness properties from fundamental elasticity theory, even using finite-element analysis.

Thus, I here offer some static and dynamic tests to help determine these properties as a function of belt length. The data can then be used in computer simulation models to optimize belt length and pre-tension to satisfy motion-control requirements.

Thus, it is an object hereof to alleviate such problems and provide at least some of the here-described features and advantages. A more particular object is to provide means for quantifying belt damping parameters—especially for various belt-lengths, yet by testing at only a few belt-length positions. Another object is to do so by subjecting the belt to sinusoidal shaking at resonance conditions.

A further object is to avoid conventional solutions, such as testing a belt in the mechanism it is to be used in.

Other objects and advantages of the present invention will be apparent to those skilled in the art.

BRIEF DESCRIPTION OF THE DRAWINGS

The foregoing and other features and advantages of the present invention will be appreciated by workers as they become better understood by reference to the following detailed description of the present preferred embodiments, these being considered in conjunction with the accompanying drawings, wherein like reference symbols denote like elements:

FIGS. 3A, 3B give related analysis.

PRELIMINARY DISCUSSION

Before describing my preferred test methods and equipment, the following gives my ideas on how stiffness and damping will be involved.

Stiffness Characteristics:

Belt stiffness is a key piece of data needed for a comprehensive analysis, for instance, where synchronous belts are concerned (such as are increasingly used for control of high-speed motion). Note: for simulating performance of a system, before building it, one should secure data on a belt's stiffness and damping characteristics.

Figure 5:
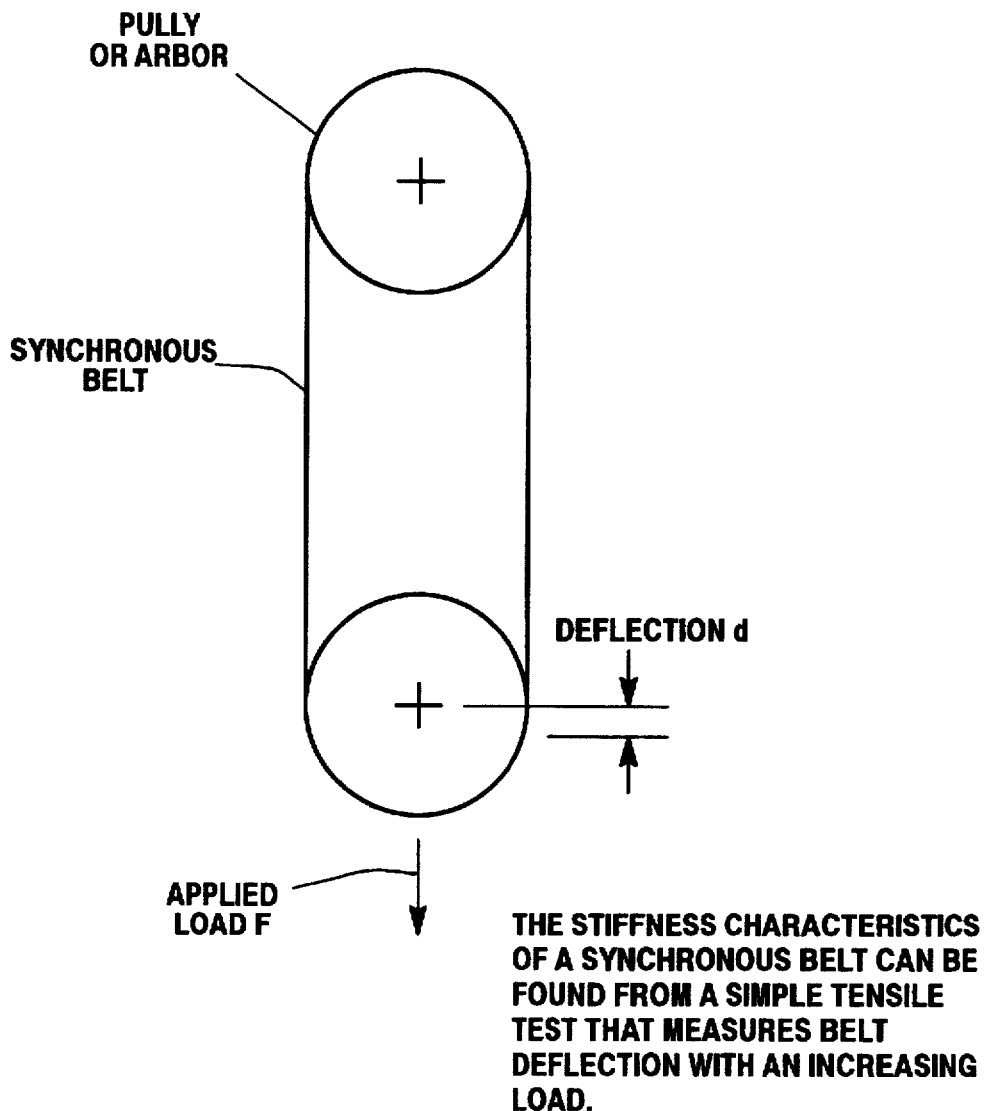
FIG. 5 schematically depicts a Force vs Deflection test set-up (tensile test), to determine stiffness, while FIG. 6 plots related typical Force vs Deflection characteristics.
Figure 6:
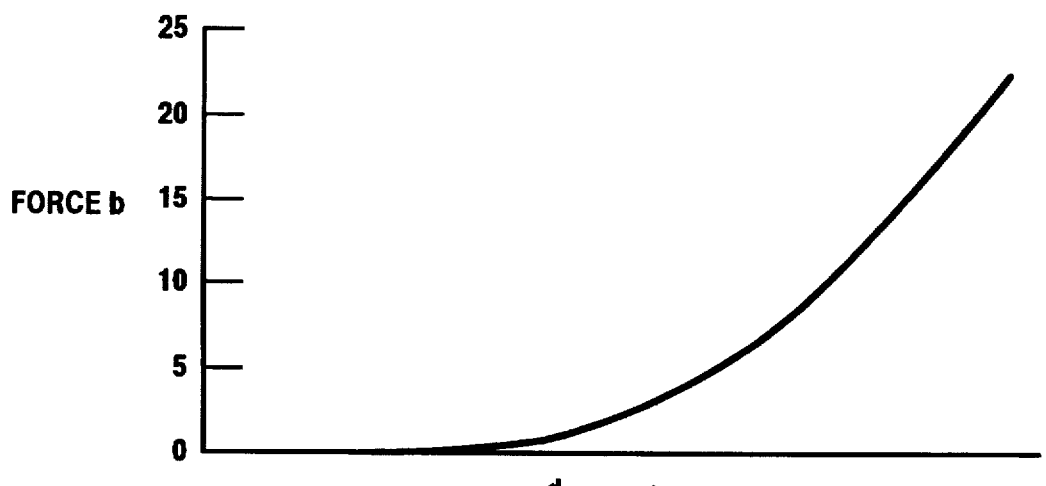

Belt stiffness can be approximated by analysis, e.g., of data found using a simple tensile test that determines force-versus-deflection characteristics of a flexible, synchronous belt (e.g., see FIGS. 5, 6—in FIG. 5, deflection vs increasing load is measured to determine stiffness—with FIG. 6 giving a related non-linear force/deflection curve). This can be performed with commercial tensile testers or with fixtures built in-house using grooved pulleys or even simple arbors. The goal is to measure the change in center distance between pulleys while applying a load. Data collected while gradually increasing load produces static force-deflection characteristics (e.g., see FIGS. 5, 6).

Most deflection takes place in the belt segments between the pulleys, assuming there is a significantly greater length between pulleys than wrap around them. When this is true, each belt segment can be approximated as a simple tensile element that has the mathematical relationship $$\frac{F}{d} = \frac{AE}{L}$$

where F=force, d=deflection, L=length, and AE=equivalent cross-sectional area multiplied by the modulus of elasticity.

An advantage of looking at belt stiffness with this equation is that it needs only one test to calculate stiffness values for belts of varying lengths. The test does not obtain precise values for A and L because the belt is a composite material. However, there are not many kinds of belt constructions and a designer only needs to know the product AE for a given construction and width. AE values of differing widths of similar construction can be readily estimated. When calculating AE for other widths, care must be taken to ensure the number of cords is proportional to width.

The test produces a force-versus-deflection curve that is nonlinear, especially at low forces and deflections. This means the equivalent AE value is nonlinear with deflection (e.g., see FIG. 6 plot for a 0.5-in. wide, 38-in. long belt with a 0.080 pitch and Kevlar cords. A quadratic or cubic polynomial generally fits this curve well. A commercial computer program may perform the curve-fitting calculations that give the polynomial coefficients).

This representation of belt stiffness is easily implemented into a computer program that simulates mechanisms or complete servosystems.

The nonlinear behavior of the force-versus-deflection curve brings out two important points about synchronous belts.

First, initial tension needed to prevent "jumping" pulley teeth during dynamic torque loading is less than one might first calculate. When applying a torque load to the driven pulley, absolute deflection of both belt segments must be the same. The segment that stretches experiences a large tension increase. However, the other segment experiences only a small tension decrease—smaller than if the belt had linear force-versus-deflection characteristics. This means a lower initial tension can be used, increasing belt life and reducing acoustic noise.

Second, a synchronous belt has low stiffness at low initial tension. When driving significant inertias, in servosystems, this small stiffness may result in system resonant frequencies low enough to affect stability. When this is the case, appropriate filtering should be applied to limit bandwidth of the servosystem, or initial tension be increased to maintain desired bandwidth.

Damping Characteristics:

Another key bit of information needed for predicting motion-control performance is the belt's damping characteristics. One method to obtain this data is to test the synchronous belt on a "shake table" according to a feature of this invention.

Figure 7:
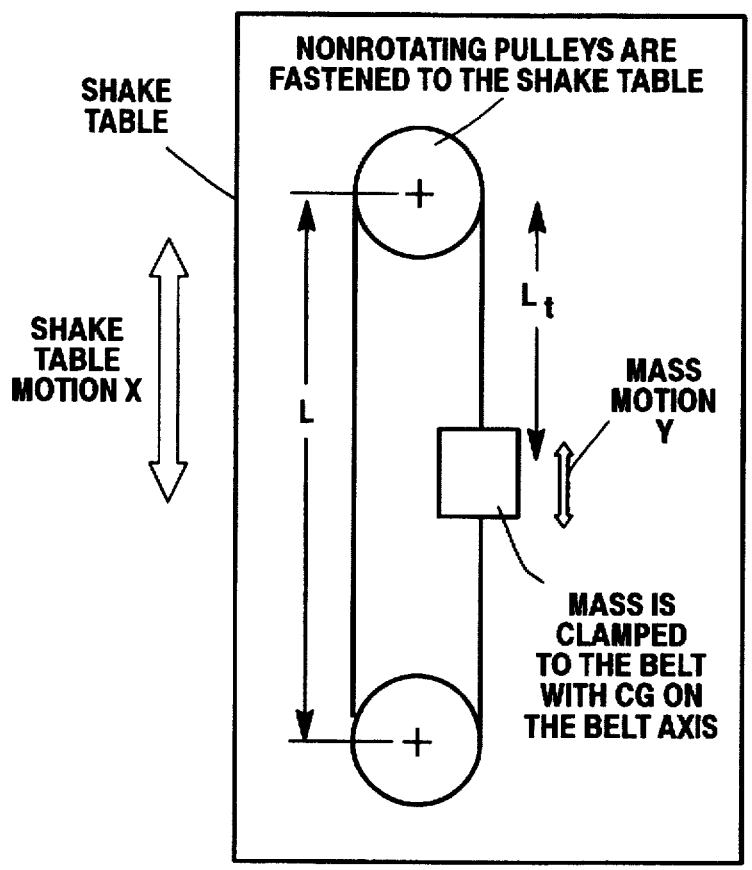
FIG. 7 is a showing like that in FIG. 1 of a test fixture for determining belt damping.

In this setup (e.g., see FIG. 7 and related embodiment in FIG. 1, described below), nonrotating pulleys with a fixed center-to-center separation distance are mounted on a shale table. After tensioning the belt, the pulleys are locked to the frame and a mass is attached to one segment of the belt with its center-of-gravity on belt axis.

With the setup complete, the shake table applies a steady-state, sinusoidal motion (e.g., see arrow Y) to the rigid frame. The motions of the frame (arrow X) and mass (arrow $L_y$) are monitored, usually with accelerometers. The frequency of the applied sinusoidal motion is varied until the mass-and-belt system resonates. From fundamental vibration theory, only damping forces limit the motion of a system driven at resonance, as expressed:

$$F_n = -mw^2 X + jcw X + kX$$

where $F_n$=applied sinusoidal force amplitude, X=displacement amplitude, and $j$ $\sqrt{-1}$. At resonance, $$\omega = \frac{k}{m}$$

Therefore, the spring force kX cancels the inertia force $m\omega X$, leaving only the damping force, $c\omega X$.

Because damping in synchronous belts is relatively large, driving a belt at resonance generally does not produce destructive forces. The system need only be driven at resonance for a short time to record the frame and mass motions.

While this damping force, and the damping in the belt, is easily determined from elementary vibration theory, changing to another length of belt would require another test. Thus, it is desirable to obtain damping properties in a manner similar to the method for finding stiffness, so that damping for belts of different lengths and widths can be readily estimated without tedious, time-consuming fixture building and testing.

My Novel Approach:

According to a feature hereof, one can accomplish this as follows:

Visualize the belt as a bar that has a simple stress-strain relationship. To include damping, assume the simple relationship that stress $\sigma$ is proportional to strain $\epsilon$, and also proportional to the change in strain with respect to time:

$$\sigma = \epsilon E + c_d \frac{\partial \epsilon}{\partial t}$$

The latter proportionality constant would be a value representing material damping properties analogous to Young's modulus being proportional to strain. Certainly for small deflections this is a reasonable assumption. Solving this equation for a step input force and assuming average stress equals force divided by area, gives:.

$$c = AQL$$

where c=damping coefficient, L=length, and AQ equivalent cross-sectional area multiplied by the material damping property.

Belt segment lengths are known from the shaker tests; AQ values can be calculated from c and L. Similar to stiffness calculations, individual values for A and Q are not needed to perform mechanism simulations.

In addition, friction between belt teeth and the pulley grooves, where the belt is tangent to the pulley, produces damping. Assume this damping is the same for each location and is independent of belt length. For example.

$$c_1 = c_t + \frac{AQ}{L_1}$$

where $c_1$ is the total damping in belt segment $L_1$: $c_t$ represents the belt-pulley interface damping coefficient; and $AQL_1$, represents the internal damping in the belt segment. The lengths in the equations for damping and stiffness are the lengths between the mass and the belt/pulley interface tangent points.

Figure 8:
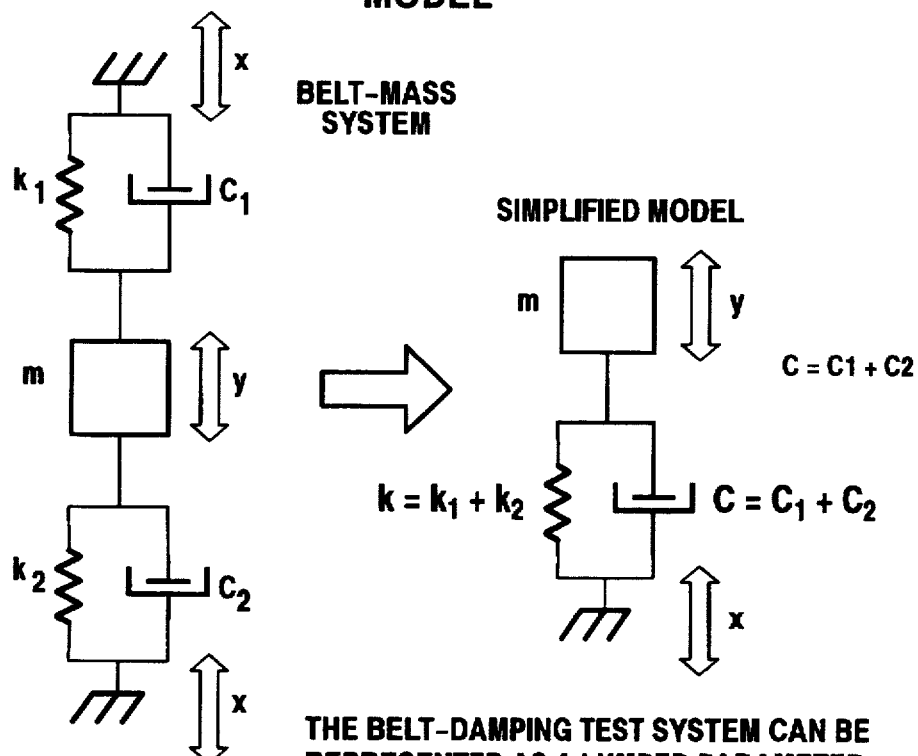
FIG. 8 gives a related "Lumped Parameter model"

The belt-damping fixture can be shown as a lumped-parameter model (e.g., see FIG. 8). The belt segment with no mass attached does not enter into the model because it does not stretch or compress during the test (cf. Table motion, arrows X; mass motion arrow y; stiffness/damping $K_1$, $C_1$ and $K_2$, $C_2$ for the belt segment). The model can be simplified, and equations for such a system are as follows:

$$\frac{y-x}{x} = \frac{r^2}{\sqrt{(1-r^2)^2 + (2\zeta r)^2}}$$

where $$r = \frac{\omega}{\omega_n}$$

$$\zeta = \frac{c}{2\sqrt{km}}$$

and $$\omega_n^2 = \frac{k}{m}$$

In the above, ω=driving frequency, $\omega_n$=natural frequency; m=mass; k=stiffness; and c=damping coefficient.

At resonance, r=1 and the overall damping coefficient c can be calculated from the mass and resonant frequency. The belt damping value Q and interface damping cannot be calculated from a single test. Moving the mass to another location along the belt and repeating the rest solves this problem. Doing so results in a different resonant frequency and, thus, a different damping value (c). The simultaneous linear equations can then be solved for the two damping values.

Figure 9:
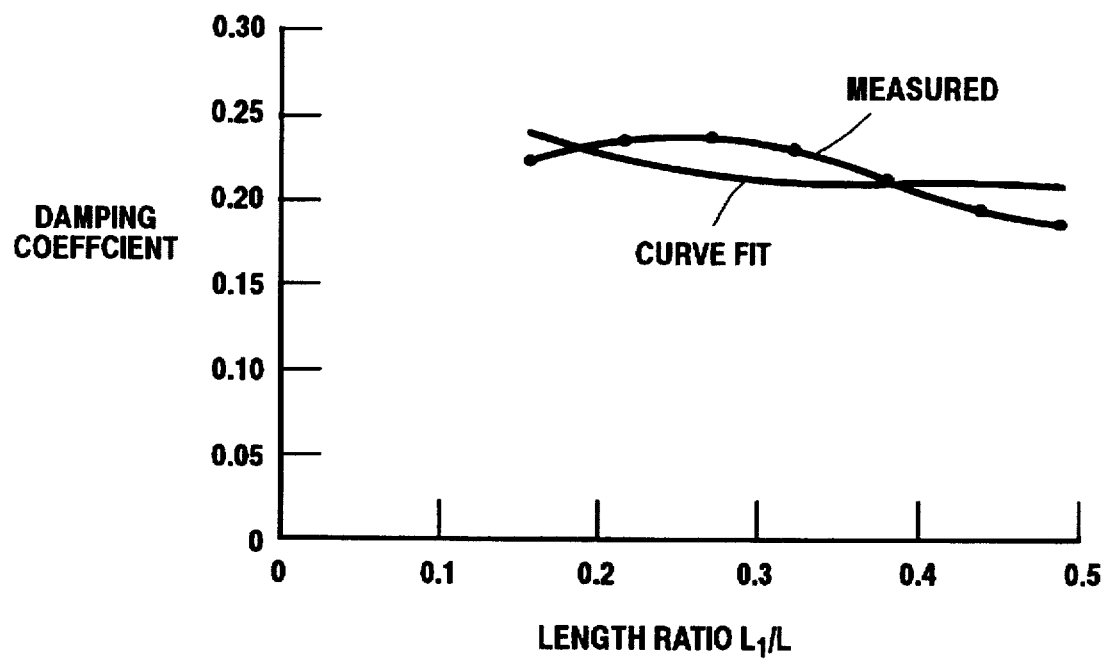
FIG. 9 gives exemplary damping vs length ratio values for a belt-with-attached-mass, under "shaking" conditions.

A more accurate method, however, repeats the test with the mass positioned at several different locations along the belt, as for curves in FIG. 9. A "curve-fitting" procedure then obtains optimal values for damping coefficients (e.g., see FIG. 9) This tends to average out the effects of measurement errors and any minor construction irregularities within the belt segment. The independent variable can be the ratio of one of the belt segment lengths to the length of belt between the pulleys.

I find that the model predicts damping coefficients within about 10% of measured values. This is good accuracy compared to that typically obtained for damping in mechanical systems. Usually the designer must provide much more margin than this in the actual device to account for manufacturing tolerances.

I conclude that: damping measured in synchronous belts indicates that systems using them should have high damping factors. Experience shows that such systems have rapid settling times and little overshoot—such evidence points to high damping factors. This makes synchronous belts good candidates for accurate, quick-response motion-control systems. These quantitative methods for evaluating belt properties enable precise simulation, before one builds and tests complete systems.

PREFERRED TEST EMBODIMENT DETAILS

Figure 1:
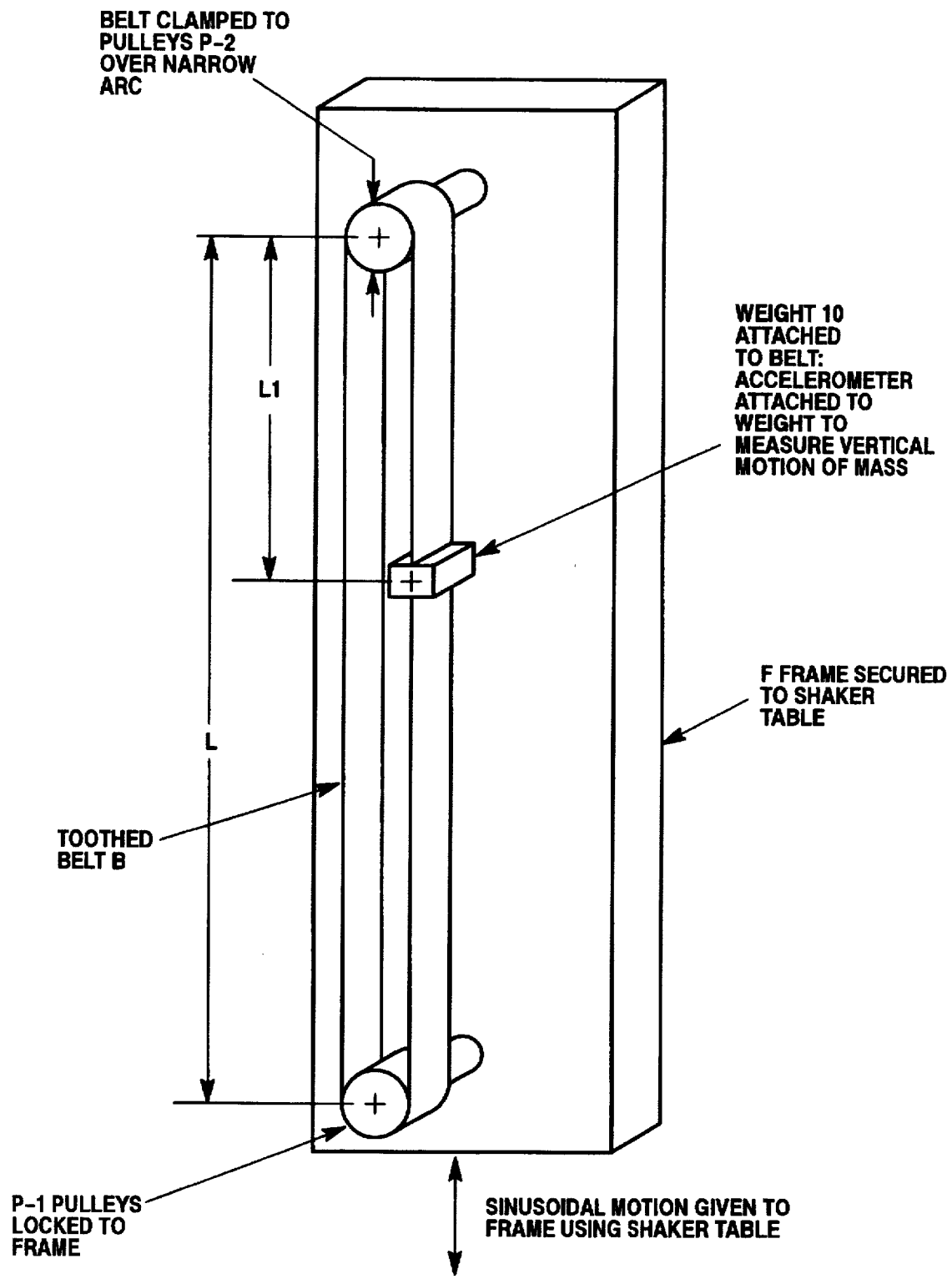
FIG. 1 is a very schematic, idealized showing of a preferred belt tensioning/shaking arrangement.

FIG. 1 shows a frame F which is relatively rigid when compared to the belt B being tested, being secured to a shaker table (not shown) adapted to experience a known sinusoidal motion. Pulleys P-1, P-2 are affixed on the frame F. A length of TOOTHED belt B (endless-loop or not; also includes any belt-like, flexible web material) is stretched over, and between, the pulleys P-1, P-2. The distance L between pulleys is adjustable so that a desired tension may be produced in belt length B. Such tensioning is well known to those practiced in the related arts. Belt B is clamped to the pulleys over a narrow arc, away from the points where the belt segments are tangent to the pulleys. This prevents gross relative motion between the belt and the pulleys.

A weight 10 of known mass (test mass m), is clamped to belt B at some known distance L1 from the center of one pulley P-2. Various known means of clamping may be used, such as a common C-clamp as known in the art. This clamp, with any needed transducer attached to it, should have its center of gravity near the (width, and thickness) axis of belt B.

Motion-Detect means MD is the transducer used for measuring the vertical motion-amplitude of mass m, either relative to the shaker table or relative to the same reference as the shaker motion. This may be accomplished by any one of many well known expedients such as: an accelerometer or like transducer (with indicator also used, if desired—see FIG. 2), or a recording pen, or a light beam reflected off the mass m onto a scale, or an electromagnetic voltage generator, etc. For illustration purposes, accelerometers will be preferred here to measure motions of both the mass m and the shaker table. Such accelerometers are well known to artisans familiar with motion transducers. For illustration purposes, these accelerometers are assumed to measure acceleration relative to the earth. Piezo-electric accelerometers are well known examples and preferred. Or, one may equivalently measure velocity or displacement, instead of acceleration, as artisans understand.

The belt and frame assembly is mounted to the shaker table so that the length L of the belt, under test, lies along the same direction as the motion of the shaker table (see arrows FIG. 1). Motion of the shaker table is transmitted to the mass m (along plane of frame F) via pulleys P-1, P-2 and belt B wound thereon.

The motion of mass m may, or may not, have the same amplitude as that of the shaker table because of the longitudinal (i.e.; tension and compression) flexibility of the belt B. Belt B and object 10 clamped thereon may be viewed as, essentially, the equivalent of a spring and mass system, having a resonant frequency $f_R$. It will be assumed that when a spring and mass system is shaken at its resonant frequency, the motion of the mass is limited only by the damping in the system. Here, belt B is assumed to provide the only significant loss of energy in this system, thus damping must be, essentially, entirely due to the (dynamic) belt stretching. Here, it will be assumed that a damping coefficient, c, in units of force per unit velocity, can be derived by the following equation:

At resonance, r=1, and equation I above becomes $$\frac{y-x}{x} = \frac{1}{2\zeta}$$

$$\zeta = \frac{c}{2\sqrt{km}} = \frac{1}{2} \cdot \frac{x}{y-x}$$

$$c = \sqrt{km} \cdot \frac{x}{y-x}$$

$$\omega_n = 2\pi f_n = \sqrt{\frac{k}{m}} \to \sqrt{k} = 2\pi f_n \sqrt{m}$$

$$c = 2\pi f_n m \frac{x}{y-x}$$

Where:
pi=3.14159
m: mass of the object clamped to the belt B
$f_n$: frequency of sinusoidal motion at resonance
xs: absolute value of motion amplitude for shaker table
xm: absolute value of amplitude for motion of mass m.

Figure 2:
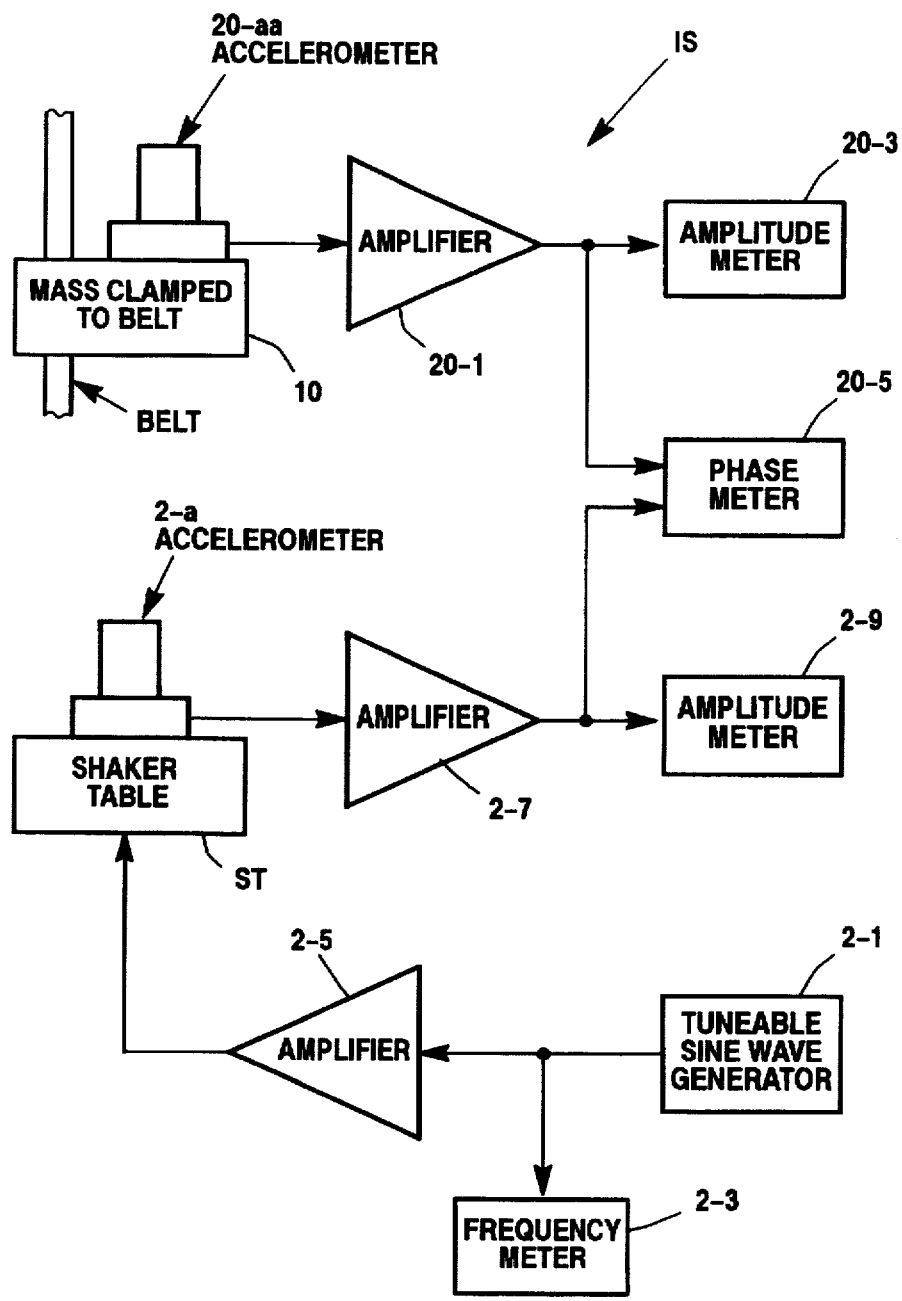
FIG. 2 illustrates a preferred measurement array for measuring belt damping for an arrangement like that of FIG. 1.

System for Measuring Damping (FIG. 2):

FIG. 2 is a block diagram of a preferred, related instrumentation system IS for determining belt damping-coefficient c. A tunable sine wave generator 2-1 is used to output a sine wave voltage at a selected frequency (this may be monitored by associated frequency meter 2-3, and this sine wave voltage from generator 2-1 may be input to an amplifier 2-5). Generator 2-1 is coupled to drive an electro-dynamic shaker table st. (This may alternatively be a electrohydraulically-driven shaker table.) The shaker table motion is preferably detected by an accelerometer 2-a (or like amplitude transducer means) whose electrical output may be fed (e.g., via an amplifier 2-7 if needed), to an amplitude meter 2-9 which may indicate the value xs (shake-amplitude for table st) if desired.

Similarly, an accelerometer 20-aa is attached to the mass m (that is clamped onto the belt, and its output may be fed to an amplifier 20-1, and then to an amplitude meter 20-3 if desired, to indicate the value xm (shake-amplitude for mass m).

In any event, each accelerometer output is fed, in common, to a phase meter 20-5, which measures the relative phase between the peaks of the (sine wave) motions of the mass and table while shaken. The tuneable sine wave generator 2-1 is adjusted until these relative phases are at 90° degrees.

This 90°-degree phase relation is here assumed to occur at "resonance". One example for so measuring phase is with the use of Lisajou figures on an oscilloscope. Another way to measure phase, as well as amplitude, is with an FFT analyzer. These devices are in common use. The frequency at which the 90°-degree phase relation occurs is, of course, resonant frequency: the value $f_R$ used in the above equation.

Note: the equation above for determining value c has no dependence on belt length. If mass m is clamped at a different position along the belt length, and the measurement process repeated, a different value of c will result. It will be shown that this should occur by reference (below) to FIG. 3 and will use this as a straight-forward "stress-strain, tension/compression bar model" to derive force-displacement equations in terms of elastic and damping parameters. When compared with the force-displacement equation for the "lumped parameter" model, FIG. 4, it will be seen that any segment of such a belt should have a damping coefficient which is inversely proportional to belt length (i.e., c~1/L).

Figure 3:
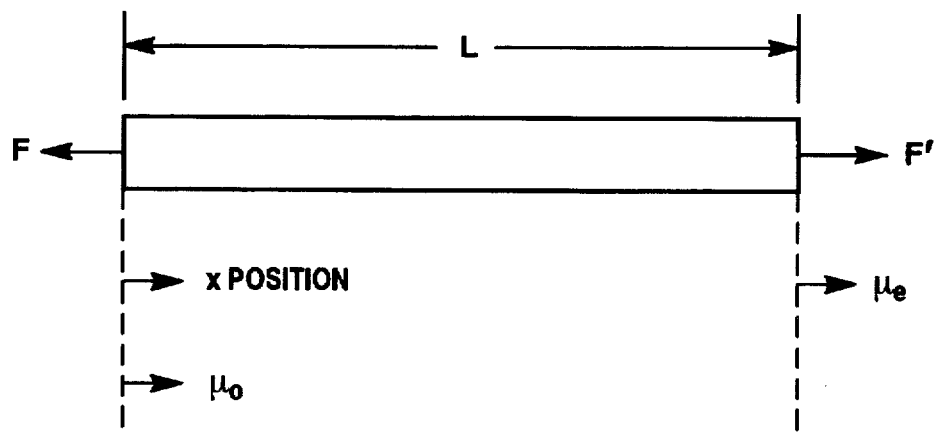
FIGS. 3 and 4 illustrate two models for related analysis.

Analysis per Tension-Compression BAR Model (FIG. 3):

FIG. 3 may be understood as a "BAR model" for analyzing forces F,F stressing a subject length of such a belt B in tension or compression. The segment will be assumed to have a length L with a test mass m disposed therealong at varied positions x, and the resultant displacements (under sinusoidal shaking at resonance) will be $U_o$, $U_e$ at respective ends.

Assuming that strain ε is defined as du/dx, a displacement U may be defined as the integral;

$$U = \int_o^x \epsilon dx + \text{a constant}$$

Stress σ is given as: σ=Eε+qdE/dt, or σ=F/A
Where
ε=elastic modulus,
q=damping coefficient for bar
t=time
A=cross-sectional area Thus, one may represent differential motion, $U_L-U_o$ as:

$$\frac{FL}{AE}(1-e^{EU/g})$$

above analysis summarized in FIG. 3A.

Workers will here understand that a belt is really a tension-compression bar model. The Test Fixture, here mentioned, yields data for a "Lumped Parameter" model (e.g., see below, and FIG. 4). The following analysis of the Lumped Parameter model shows how the measured damping data can be related to the "BAR" model.

Figure 4:
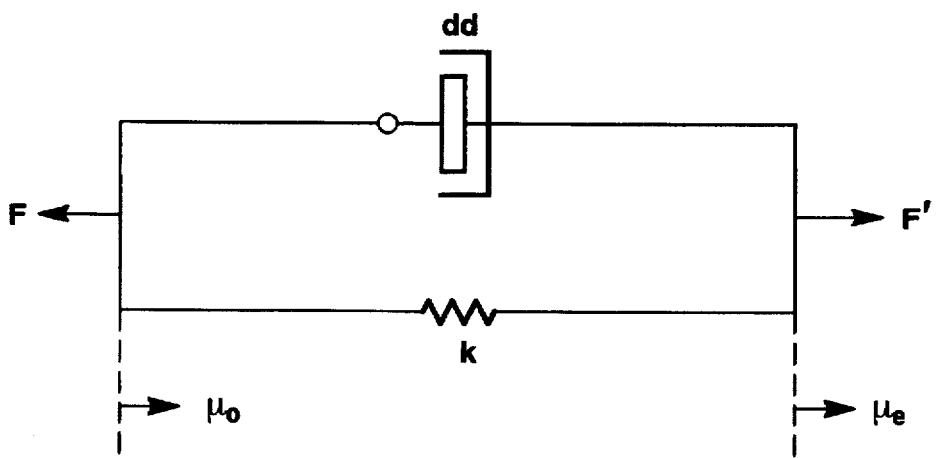
Figure 3B:
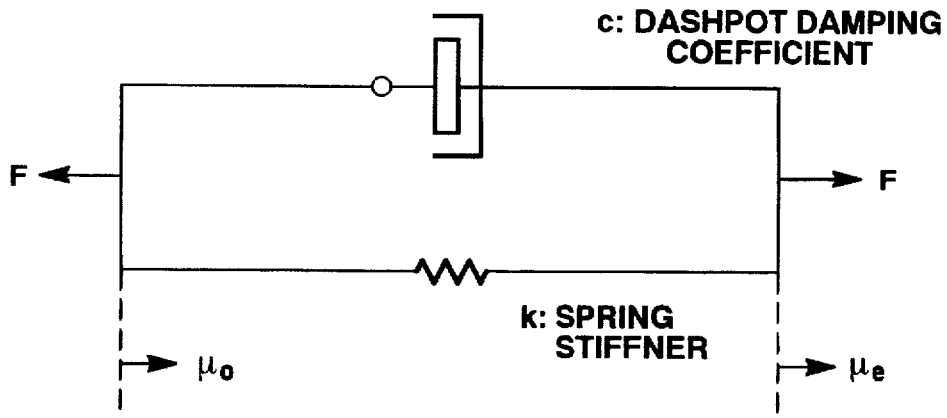

Analysis Via "Lumped-Parameter" Model (FIG. 4:

FIG. 4 may be understood as a "Lumped-Parameter" model, to be compared with the BAR model above, here, cc represents a "dashpot damping coefficient", and K: spring stiffness, with $U_o$, $U_e$ as before.

At dashpot dd, the damping force $F_{cc}$ may be expressed as:

$$F_{cc} = cc \left[ \frac{du_e}{dt} - \frac{du_o}{dt} \right]$$

At "spring" k, related force $F_k$ may be expressed as:

$$F_k = K(u_e - u_o)$$

Total force F is $F_{cc}+F_k$
Hence, the differential displacement $u_e$ is:

$$u_e - u_o = F/k(i - e^{k1/c})$$

Comparing with the BAR model:

k=AE/L c=Aq/L

Thus, damping coefficient c is inversely proportional to L, the length of belt being stretched (c~1/L).

Since the belt in FIG. 1 has two segments, L1 and L-L1, which are undergoing tension/compression, the related damping coefficient c measured is actually the sum of the two different damping coefficients: $C_2/L_1$ and $C_2/(L-L_1)$, where $C_2$=Aq. Additionally, there may be damping at the interfaces where the belt is tangent to the pulleys. This is particularly true for toothed synchronous belts where a belt tooth may rub on a pulley groove during this test. This damping is a constant, since it is not dependent on the position of the clamped mass. The measured damping coefficient c can be described as follows:

c=2* c1+c2/L1+c2/(L-L1);

or, $c=2c_1+c2/L_1+c2/L-L_1$

To obtain the damping coefficients c1 and c2, tests are run for several positions (several L1 values). If only two positions are used, then one can employ a process for solving two linear equations and two unknowns, and so calculate the constants c1 and c2. If more than two positions are used, then one of several well known "least squares, curve fitting" processes can be used to find the "best" values for c1 and c2. An example of such a process is the Marquardt-Levenbert algorithm; of course, using more test positions gives more accurate values for $c_1$ and $c_2$.

This invention will be thus understood to measure damping parameters for resilient belts such that a lumped parameter damping coefficient can be easily calculated for any length of belt (used to transmit motion from one shaft to another).

This is done, principally to determine belt damping coefficients, and so enable an accurate prediction of a belt's dynamic motion performance,—for mechanisms utilizing such belts, so that different belts can be compared for their inherent damping capability, and so that a belt can be "sized" to obtain desirable damping properties.

A salient advantage is that belt damping can be determined without actually testing the belt in the mechanism for using it. Also, one can predict damping for belts of different lengths just by testing one length of belt. A simple test fixture can be used for many different kinds and lengths of belt construction. One can also so test other resilient "belt-like" web materials, such as lengths of: photographic film, magnetic tape, ink ribbon, rope, cables, paper strips, fabric strips, etc.

Advantages Over Past Practice:

Does not require "trial-and-error" testing in the actual mechanism, and just one belt-length is needed to determine damping for many different lengths;

Does not require a specific sample size, as virtually any length belt may be used.

Does not require that the belt be permanently altered in any way; or "over-stressed" or tested in actual use environment.

Related products for using such belts or belt-like materials are: microfilm film advance mechanisms, document transports, document positioning systems, paper advance mechanisms in printers, pen plotters, magnetic and optical digital storage devices, magnetic tape recorders, printhead positioning mechanisms in typewriters and computer printers, printer ribbon advance mechanisms, optical mirror positioning mechanisms, robots, automatic assembly mechanisms, automotive alternator drives, camshaft drives, and air conditioning compressor drives, automatic adhesive tape dispensers. Such can also benefit from this invention.

In summary, the damping coefficient of a resilient web length is determined by:

1—stretching the length between a pair of pulley means, separated by distance L, and mounted on a relatively fixed frame; with a prescribed test mass m clamped thereon at distance $L_1$ from a pulley;

2—mounting the frame on a shaker table and providing a shaking means (pref. sinusoidal) to shake the frame and test mass while monitoring/adjusting the frequency thereof to arrive at resonance;

3—deriving accelerometer output (amplitude) from this table as it is shaken, while measuring this amplitude $A_r$ at resonance;

4—deriving accelerometer output (amplitude $A_m$) from this test mass m, while measuring this amplitude $A_m$ at resonance:

5—adjusting the generator to shake the table and the mass at resonant frequency $f_R$;

(e.g., doing so via phase monitor, imposing orthogonal phase-relation)

6—computing damping constant $C_1$ and $C_2$ from measurements at two or more mass positions (e.g., $L_1$);

7—and so determining a damping coefficient C according to the relation;

$$C=2C_1+C_2/L_1+C_2/(L-L_1) \text{ etc.}$$

Of course, many modifications to the preferred embodiment described are possible without departing from the spirit of the present invention. The invention is not limited to the particular types of sensors or shakers or mountings.

Accordingly, the description of the preferred embodiment should be to be considered as including all possible modifications and variations coming within the scope of the invention as defined by the appended claims.

What is claimed is:

1. A method of determining motion-control and damping characteristics for a resilient, multi-element elastomeric belt used in a prescribed servo system yet without need to test in a use environment, said method comprising the steps of:

stretching a prescribed length L of said belt between a pair of guide means mounted on frame means with prescribed tension; attaching a prescribed test weight on said length at a prescribed test-distance $L_1$ from one said guide means; shaking said frame means at resonance frequency, sinusoidally; while determining the amplitude of excursion for said weight and frame means; then changing distance $L_1$ and repeating the foregoing method steps one or more times to determine a damping characteristic.

2. The method of claim 1, used to compute ratios of distances $L_1$ vs damping coefficient.

3. The method of claim 2, using a "Lumped Parameter" technique.

4. The method of claim 1, used to calculate damping for various distances $L_1$, then solving for all distances via simultaneous equations.

5. The method of claim 1, used to calculate damping for various distances $L_1$ and then determining overall damping via curve-fitting.

6. The method of claim 1, including calculating for ratios $L_1L$ for various distances.

7. The method of claim 5, including calculating for ratios $L_1/L$ for various distances.

8. A method of testing a resilient multi-part motion-transmitting belt for damping and related motion-control characteristics yet without placing the belt into a use environment, this method comprising:

mounting a pair of rotor-guides on a frame at separation L and threading and stretching a length of said belt therebetween, while attaching a prescribed test mass m on the belt at a test distance $L_1$ from one of said rotor-guides; shaking said frame sinusoidally at resonance frequency, while measuring resonance-excursion distance for said frame and said mass; then changing said test distance $L_1$ and repeating the foregoing, operations method steps until at least one of said characteristics are derived.

9. The method of claim 8, used to compute ratios of distances $L_1$ vs damping coefficient.

10. The method of claim 9, using a "Lumped Parameter" technique.

11. The method of claim 8, used to calculate damping for various distances $L_1$, then solving for all distances via simultaneous equations.

12. The method of claim 8, used to calculate damping for various distances $L_1$ and then determining overall damping via curve-fitting.

13. The method of claim 8, including calculating for ratios $L_1/L$ for various distances.

14. The method of claim 12, including calculating for ratios $L_1/L$ for various distances.

15. The method of claim 8, wherein said distance $L_1$ is varied N times, with a damping coefficient determined for each distance $L_1$.

16. The method of claim 15, wherein said frame is affixed on shake-surface means, and controllable shaking means is applied to so shake said frame and surface means at resonance frequency.

17. The method of claim 16, wherein said shaking is controlled to execute sinusoidal shake vibration.

18. The method of claim 17, wherein the resonant amplitudes of said surface means and said test mass m are derived.

19. The method of claim 18, wherein accelerometer means and transducers are used to indicate said amplitudes.

20. The method of claim 19, wherein phase is monitored to determine resonance.

21. The method of claim 20, wherein a number of different mass-distances $L_1$ are selected and said damping co-efficient is determined for each said distance, with an overall damping coefficient for the belt derived.

22. The method of claim 8, wherein said belt comprises a servo belt for transmitting motion.

23. The method of claim 22, wherein shaking is performed by tunable sine-wave generator means.

24. The method of claim 21, wherein a damping coefficient C is derived according to the relation:

$$c = 4\pi m f_R \frac{xs}{xm - xs}$$

Where:
$\pi = 3.14159$
m: mass of the object clamped to the belt
$f_R$: frequency of sinusoidal motion at resonance
xs: absolute value of motion amplitude for shaken frame
xm: absolute value of amplitude for motion of mass m.

* * * * *